United States Patent
Govari et al.

(10) Patent No.: US 11,040,208 B1
(45) Date of Patent: Jun. 22, 2021

(54) DISTRIBUTED CARDIAC PACING SYSTEM

(71) Applicant: BIOSENSE WEBSTER (ISRAEL) LTD., Yokneam (IL)

(72) Inventors: Assaf Govari, Haifa (IL); Vadim Gliner, Haifa (IL); Alon Boumendil, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 84 days.

(21) Appl. No.: 16/716,719

(22) Filed: Dec. 17, 2019

(51) Int. Cl.
*A61N 1/368* (2006.01)
*A61N 1/37* (2006.01)

(52) U.S. Cl.
CPC ....... *A61N 1/36843* (2017.08); *A61N 1/3702* (2013.01); *A61N 1/3706* (2013.01)

(58) Field of Classification Search
None
See application file for complete search history.

(56) References Cited

U.S. PATENT DOCUMENTS

| | | | |
|---|---|---|---|
| 5,711,305 A * | 1/1998 | Swanson | A61B 5/287 600/510 |
| 5,792,064 A * | 8/1998 | Panescu | A61B 18/1492 600/510 |
| 7,526,342 B2 | 4/2009 | Chin | |
| 8,623,010 B2 | 1/2014 | Ocel | |
| 8,923,959 B2 | 12/2014 | Boveja | |
| 10,335,051 B2 | 7/2019 | Harlev | |
| 2007/0021679 A1 | 1/2007 | Narayan | |
| 2013/0041235 A1 | 2/2013 | Rogers | |
| 2018/0235692 A1 | 8/2018 | Efimov | |

* cited by examiner

*Primary Examiner* — Brian T Gedeon

(57) ABSTRACT

An apparatus includes a relay and sampling unit, a pacing unit, a pacing detection circuit, and a processor. The relay and sampling unit receives multiple electrocardiogram (ECG) signals that are sensed by respective electrodes in a heart of a patient, and digitize a first subset of the ECG signals, and forward a second subset of the ECG signals un-digitized over analog lines. The pacing unit outputs pacing signals, which the pacing detection circuit detects and outputs a trigger in response. The processor receives the trigger and identities of ones of the electrodes via which the pacing signals are to be applied, and, in response to identifying that the electrodes, via which the pacing signals are to be applied, are currently associated with the digitized ECG signals, instructs the relay and sampling unit to switch the identified electrodes to the analog lines for transferring the pacing signals.

6 Claims, 3 Drawing Sheets

DISTRIBUTED CARDIAC PACING SYSTEM

FIELD OF THE INVENTION

The present invention relates generally to the manipulation of electrophysiological signals, and more particularly to the pacing of intracardiac electrophysiological signals using a catheter.

BACKGROUND OF THE INVENTION

Various techniques were proposed in the patent literature for pacing and measuring intracardiac electrophysiological signals. For example, U.S. Pat. No. 10,335,051 describes a cardiac mapping method including measuring cardiac beats in signals at one or more electrodes on a catheter in response to electrical activity in the heart cavity and collecting a plurality of additional data signals related to the cardiac beats. A criterion is computed and is used to characterize beat morphology of a cardiac beat in the plurality of additional data signals, the criteria based on a comparison of the plurality of additional data signals and a beat template. In some embodiments, cardiac pacing is used during the mapping procedure.

As another example, U.S. Patent Application Publication 2018/0235692 describes a high resolution, multi-function, conformal electronics device generally having a flexible and stretchable, high-density electrode array, integrated with a catheter (e.g., balloon catheter) for mapping, ablating, pacing and sensing of cardia tissue associated with heart arrhythmias. The present invention can precisely locate the source of arrhythmia as described above and deliver therapy from the same electrode array. This is achieved using a capacitive sensing electrode array that can not only monitor but also deliver electrical stimulation.

SUMMARY OF THE INVENTION

An exemplary embodiment of the present invention provides an apparatus including a relay and sampling unit, a pacing unit, a pacing detection circuit, and a processor. The relay and sampling unit is configured to receive multiple electrocardiogram (ECG) signals that are sensed by respective electrodes in a heart of a patient, to digitize a first subset of the ECG signals, and to forward a second subset of the ECG signals un-digitized over analog lines. The pacing unit is configured to output pacing signals. The pacing detection circuit is configured to detect the pacing signals and to output a trigger in response to the pacing signals. The processor is configured to: (a) receive (i) the trigger and (ii) identities of ones of the electrodes via which the pacing signals are to be applied, and (b) in response to identifying that the electrodes, via which the pacing signals are to be applied, are currently associated with the digitized ECG signals, to instruct the relay and sampling unit to switch the identified electrodes to the analog lines for transferring the pacing signals.

In some exemplary embodiments, the apparatus further includes a patient interface unit (PIU), which is configured to accept and store the identities of the electrodes via which the pacing signals are to be applied, and wherein the processor is configured to, once triggered by the pacing detection circuit, read the identities from the PIU.

In some exemplary embodiments, the relay and sampling unit is included in a dongle that connects the electrodes to the PIU.

In an exemplary embodiment, the pacing detection circuit is further configured to detect that the pacing signals stopped, and in response trigger the processor, and wherein the processor is further configured, once triggered, to command the relay and sampling unit to switch the selected electrodes from the analog lines to digital lines.

There is additionally provided, in accordance with another exemplary embodiment of the present invention, a method including, in a relay and sampling unit, receiving multiple electrocardiogram (ECG) signals that are sensed by respective electrodes in a heart of a patient, digitizing a first subset of the ECG signals, and forwarding a second subset of the ECG signals un-digitized over analog lines. Pacing signals are outputted using a pacing unit. The pacing signals are detected and in response to the pacing signals a trigger is outputted. In a processor received are (i) the trigger and (ii) the identities of the electrodes via which the pacing signals are to be applied. In response to identifying that the electrodes, via which the pacing signals are to be applied, are currently associated with the digitized ECG signals, the relay and sampling unit are instructed to switch the identified electrodes to the analog lines for transferring the pacing signals.

In some exemplary embodiments, the method further includes, upon detecting that the pacing signals stopped, the selected electrodes being switched from the analog lines to digital lines.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
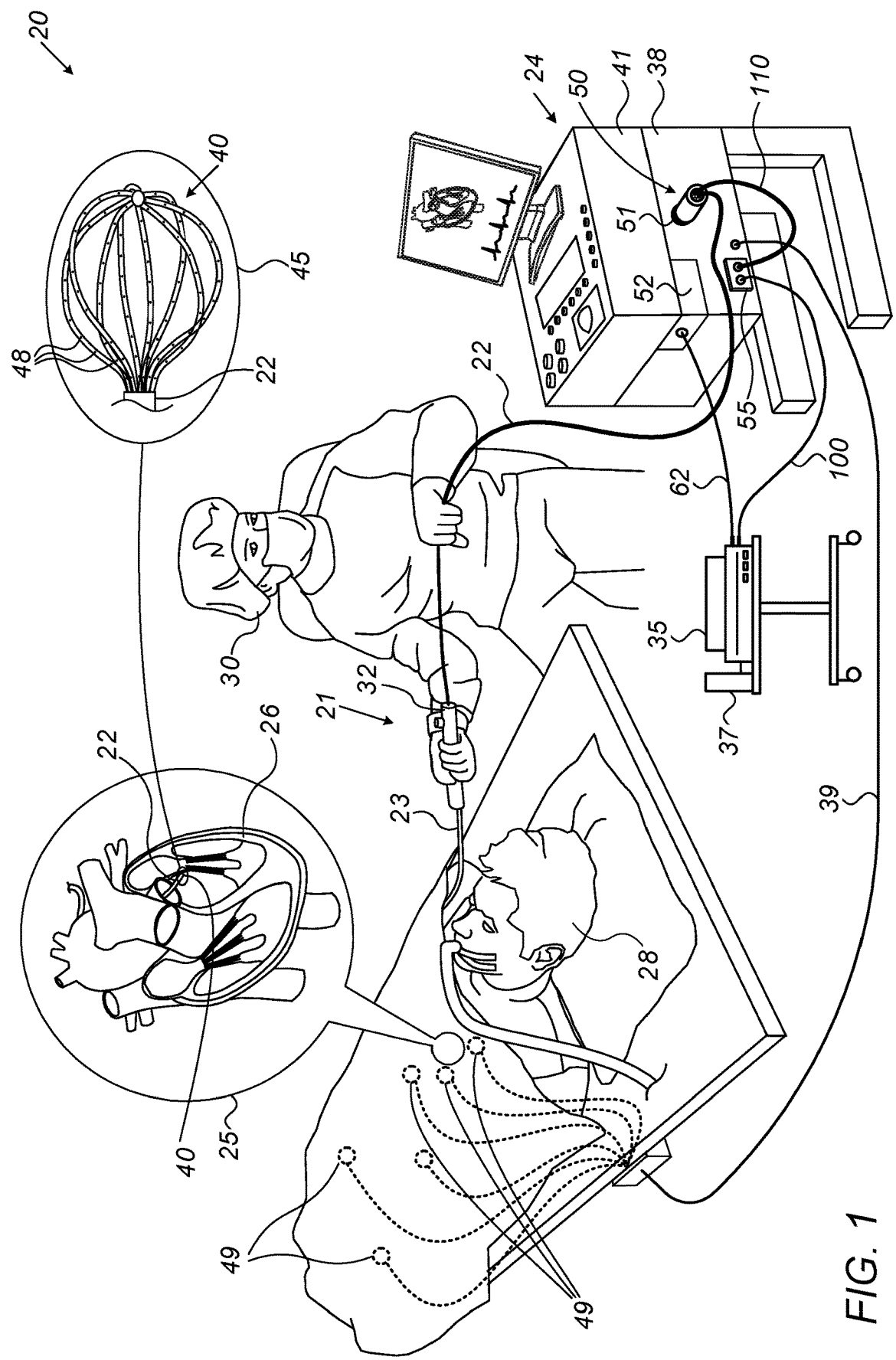
FIG. 1 is a schematic, pictorial illustration of a catheter-based cardiac pacing and electrophysiological sensing system, in accordance with an exemplary embodiment of the present invention.

Pacing a heart using analog catheter-based systems is relatively straightforward, as such systems have lines that can directly conduct the pacing signals between a pacing unit connected to the system and the catheter. Typically, the pacing is performed by selecting conducting lines (corresponding to the desired catheter electrodes) and transmitting pacing signals along the selected lines, where automatic pacing enablement is readily provided by control circuitries of the analog system.

Unfortunately, such legacy analog catheter-based cardiac systems are usually able to measure only a limited number of signals, e.g., up to several tens of electrocardiogram (ECG) channels of analog signals acquired by the same number of electrodes (called hereinafter also "analogically connected subset of electrodes," which is set to acquire a second subset of the ECG signals un-digitized, wherein a first set of the ECG signals is digitized to overcome shortage in analog lines).

Modern diagnostic catheters, however, may have many more electrodes, e.g., 256 electrodes, inside a heart of a patient. To accommodate the extra channels of modern diagnostic catheters, signals from such a catheter (e.g., a 256-channel basket catheter) may be transmitted to a legacy catheter-based system via a digital communication link. Electrodes that are connected via the digital line are called hereinafter also "digitally connected subset of electrodes," which is set to acquire a first subset of the ECG signals that are digitized to overcome shortage in analog lines.

To use the digital link to, for example, transmit signals from the digitally connected subset of electrodes to an ECG recording device, a dongle comprising analog to digital circuitry may be inserted between the diagnostic catheter and the legacy recording device. A display of the system may present such digitally transmitted ECG signals.

For pacing, however, the dongle and the digital line cannot support a delivery of analog signals (e.g., application of stimulating signals using a pacing unit) via electrodes selected from the digitally connected subset of electrodes.

Exemplary embodiments of the present invention that are described hereinafter enable pacing from an electrode pair selected from either the analogically or the digitally connected subset of the electrodes the catheter.

In some exemplary embodiments, a pacing apparatus is provided that comprises a relay and sampling unit, a pacing unit, a pacing detection circuit, and a processor. The relay and sampling unit are configured to receive multiple electrocardiogram (ECG) signals that are sensed by respective electrodes in a heart of a patient (e.g., by being disposed a catheter inserted into the heart), to digitize a first subset of the ECG signals, and to forward a second subset of the ECG signals un-digitized over analog lines. The pacing unit, configured to output pacing signals, while the pacing detection circuit is configured to detect the pacing signals and to output a trigger in response to the pacing signals. The processor is configured to (a) receive (i) the trigger and (ii) the identities of the electrodes via which the pacing signals are to be applied, and (b) in response to identifying that the electrodes, via which the pacing signals are to be applied, are currently associated with the digitized ECG signals, to instruct the relay and sampling unit to switch the identified electrodes to the analog lines for transferring the pacing signals.

In an exemplary embodiment, the physician selects the electrodes using a patient user interface (PIU). If the selected electrode pair are currently associated with the digitized ECG signals (i.e., belongs to the digitally connected subset of electrodes), the PIU updates the processor with the identity of the electrodes (e.g., with a running index between 1 and 256). Pacing signals are generated as usual by the pacing units, but they are transmitted over the dedicated analog line that is used only for connecting to the otherwise digitally connected subset of electrodes. The pacing detection circuit detects the pacing signals conducted on the dedicated line and triggers the processor. Upon being triggered, the processor commands the relay and sampling unit, also called hereinafter "switching assembly," to switch the selected electrode pair to an analog input in the switching assembly (e.g., using existing relays in the switching assembly) to which the dedicated analog pacing line is connected, in order to enable pacing.

In an exemplary embodiment, the switching assembly is included in a dongle that connects the electrodes to the PIU.

In another exemplary embodiment, once pacing ends, the pacing detection circuit detects the event and triggers the processor to command the dongle to switch the selected electrodes from the analog input back to the digital line.

Typically, the processor is programmed in software containing a particular algorithm that enables the processor to conduct each of the processor-related steps and functions outlined above.

The disclosed technique provides a simple and effective means to enable the legacy system to pace cardiac tissue using any electrode of multiple electrodes of a modern catheter. Furthermore, the disclosed technique may be used with other catheters, such as brain catheters that apply and measure electrophysiological signals related to brain activity. Thus, the disclosed technique may increase the availability of several categories of modern catheter-based diagnostic services.

System Description

FIG. 1 is a schematic, pictorial illustration of a catheter-based cardiac pacing and electrophysiological sensing system 20, in accordance with an exemplary embodiment of the present invention. System 20 may be, for example, a CARTO® 3 system, produced by Biosense-Webster, Irvine, Calif. As seen, system 20 comprises a catheter 21, having a shaft 22 that is navigated by a physician 30 into a heart 26 of a patient 28. In the pictured example, physician 30 inserts shaft 22 through a sheath 23, while manipulating shaft 22 using a manipulator 32 near the proximal end of the catheter.

In the exemplary embodiment described herein, catheter 21 may be used for any suitable diagnostic purpose, such as cardiac pacing, using pacing unit 37, and electrophysiological mapping of heart 26. As shown in inset 25, a distal end of shaft 22 of catheter 21 is fitted with a multi-electrode basket catheter 40. Inset 45 shows an arrangement of multiple sensing electrodes 48 (i.e., 256 or more channels) of basket catheter 40. The proximal end of catheter 21 is connected by a dongle 50 to a control console 24.

An ECG recording instrument 35 may receive various analog ECG signals sensed by the analogically connected subset of electrodes 48 during the process and transmitted via legacy line 62. Digital ECG signals that are sensed using the digitally connected subset of electrodes 48, however, can only be presented on a display of console 24.

Similarly, in system 20, there is no analog link between a digitally connected subset of catheter 21 electrodes 48 and pacing unit 37, since legacy cable 62, between control console 24 and recording instrument 35 and pacing unit 37, supports only a limited number of electrodes that are selected as belonging to an analogically connected subset of electrodes.

A dedicated compound line is provided to enable a pacing unit to pace from electrodes belonging to the digitally connected subset of electrodes. In the illustrated exemplary embodiment, the compound line comprises (a) an analog pacing line 100 between pacing unit 37 and a pacing-detection circuit 55, and, (b) an analog pacing link 110 between circuit 55 and dongle 50. When pacing from a digitally connected subset of electrodes is required, circuit 55 triggers processor 41 to command relays 51 inside dongle 50 to switch the selected electrodes into an analog input of dongle 50 to which line 100 is connected. Responsively, relays 51 inside dongle 50 switch the routing of pacing analog signals to the electrodes of the selected digitally connected electrodes, as further described in FIG. 2.

Console 24 comprises a processor 41, typically a general-purpose computer, with suitable front end and interface circuits 38 comprising a patient interface unit (PIU) 52 for (a) receiving analog and digital ECG signals from dongle 50, as well as non-ECG signals (such as position signals) from sensing-electrodes 48 of catheter 21, and (b) selecting catheter electrodes from which pacing will be applied to tissue.

Electrodes 48 may include 256 or more sensing n electrodes. Each electrode of electrode 48 is referenced as "electrode 48 #1, #2, #3 . . . #n" disposed inside or near the heart. For this purpose, processor 41 is connected to sensing electrodes 48 via wires running within shaft 22. Interface circuits 38 are further configured to receive ECG signals as well as non-ECG signals from surface body electrodes 49. Typically, electrodes 49 are attached to the skin around the chest and legs of patient 28. Processor 41 is connected to electrodes 49 by wires running through a cable 39 to receive signals from electrodes 49.

Processor 41 is typically programmed in software to carry out the functions described herein. The software may be downloaded to the processor in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 3, that enables processor 41 to perform the disclosed steps, as further described below.

Distributed Cardiac Pacing System

Figure 2:
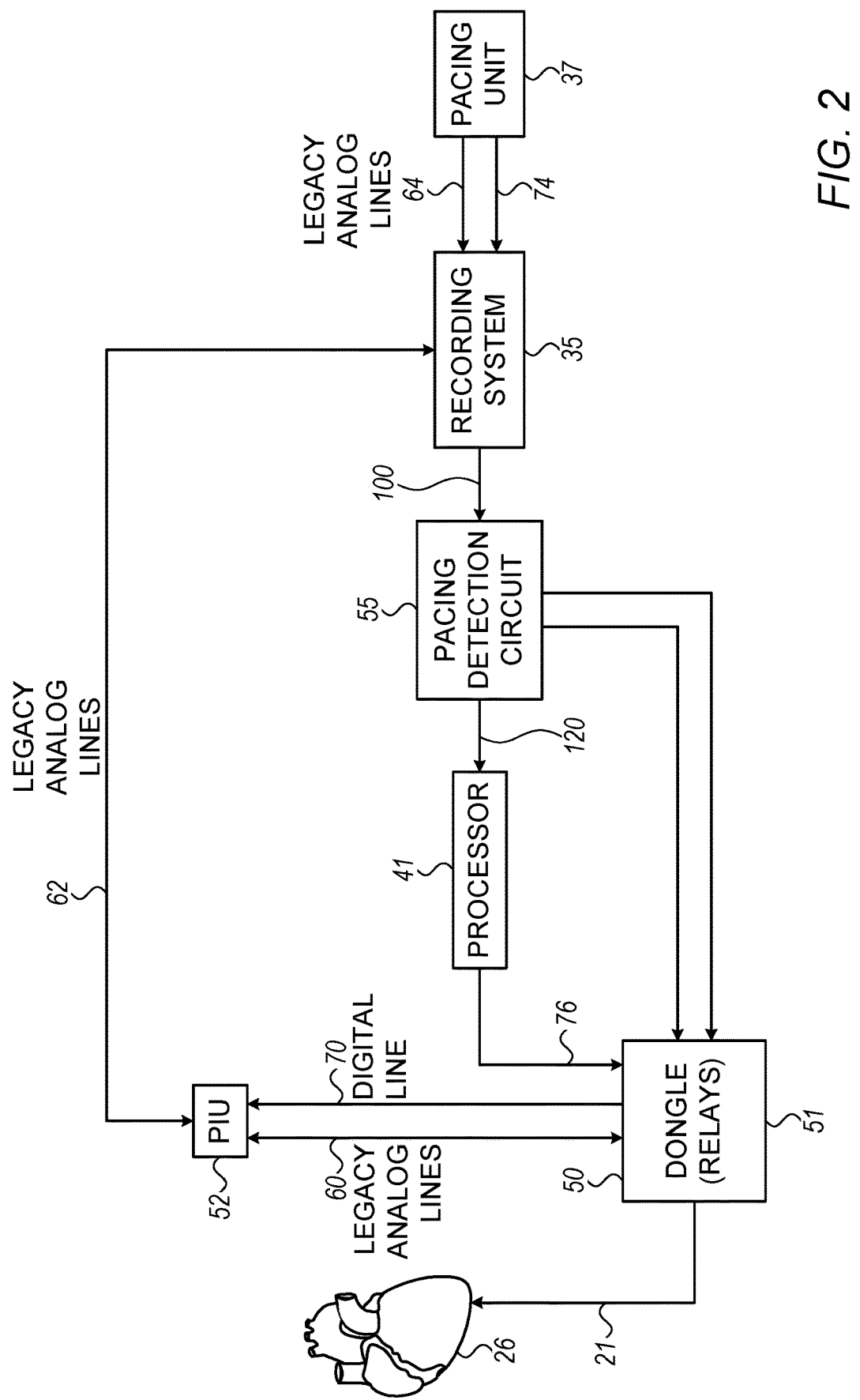
FIG. 2 is a block diagram of the cardiac pacing and electrophysiological sensing apparatus of the system of FIG. 1, in accordance with an exemplary embodiment of the present invention.

FIG. 2 is a block diagram of the cardiac pacing and electrophysiological sensing apparatus of system 20 of FIG. 1, in accordance with an exemplary embodiment of the present invention.

As seen, catheter 21 of system 20 is connected to dongle 50, where a distal end of catheter 21 is inserted into heart 26 to sense electrophysiological signals and/or to pace cardiac tissue. All of electrodes 48 of catheter 21 may acquire or apply analog signals, however there are not enough available (e.g., existing) analog lines 60 in system 20 to connect all electrodes 48 to PIU 52 of console 24.

As further seen in FIG. 2, dongle 50 routes legacy analog lines 60 to PIU 52 for use with a subset of electrodes 48 that are chosen to be analogically connected. Dongle 50 is further connected to PIU 52 with a digital line 70, via an ADC inside dongle 50, for PIU 52 to receive signals from the remining digitally connected subset of electrodes 48.

Two of catheter electrodes 48 are selected for pacing. The two pacing electrodes may be selected by a user interface of PIU 52, and the identity (e.g., the running index) of the selected electrodes is communicated from PIU 52 to processor 41 of console 24. If the two selected electrodes belong to the analogically connected subset of electrodes 48, then these are already routed by a compound analog line 60-62-64 to recording system 35 and to pacing unit 37. PIU 52 is configured, upon command by a user, to enable pacing from unit 37 via the compound analog line (i.e., using in-series lines 60, 62, and 64). This configuration is already configured in legacy system 20 to command relays 51 in dongle 50 to switch to the selected pacing electrodes to channel the pacing signals using compound line 60-62-64 to heart 26.

However, if the two selected electrodes belong to the digitally connected subset of electrodes 48, PIU 52 can only provide the identity of the electrodes to processor 41. To pace via the selected electrodes, a dedicated compound line 74-100-110 from pacing unit 37 to dongle 50 is used by the user.

An analog pacing signal in line 74 is routed via recording system 35 through analog line 100 to pacing detection circuit 55. Circuit 55 routes the signal via two dedicated lines 110 comprising two single conductor lines. Furthermore, upon sensing an analog pacing signal, circuit 55 triggers (120) processor 41, via a line 76, to send a command to dongle 50 to switch relays 51 to physical inputs of dongle 50 that are wired to line 110. Responsively, dongle 50 switches the selected electrodes so as to channel the pacing signals running in line 110 to heart 26.

The example configurations shown in FIGS. 1 and 2 are chosen purely for the sake of conceptual clarity. In alternative embodiments, the disclosed techniques may use other suitable configurations comprising other wiring schemes, different standalone interfaces and switching devices, and catheter types other than basket catheters.

Figure 3:
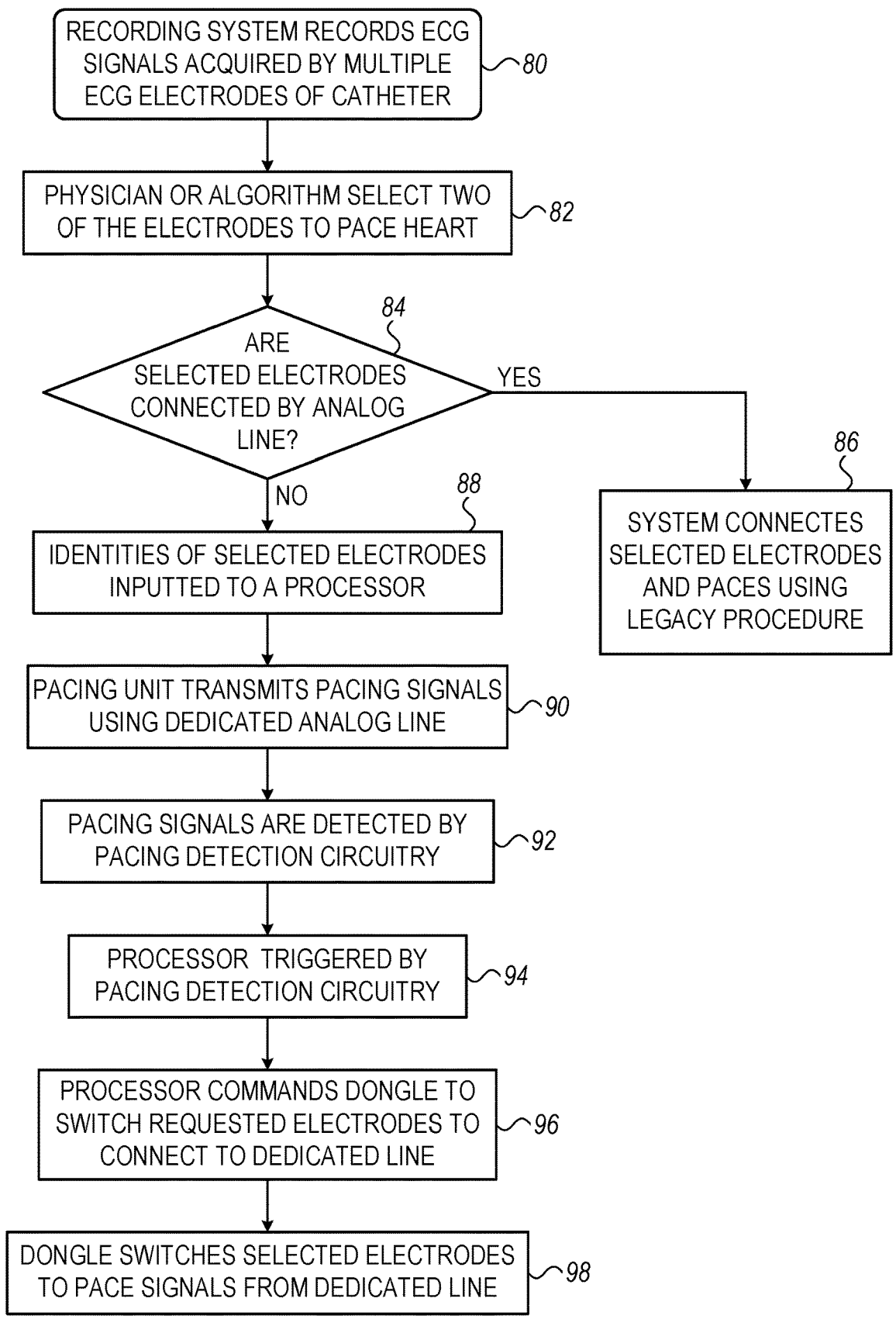
FIG. 3 is a flow chart that schematically illustrates a method for pacing using the apparatus of FIG. 2, in accordance with an exemplary embodiment of the present invention.

FIG. 3 is a flow chart that schematically illustrates a method for pacing using the apparatus of FIG. 2, in accordance with an exemplary embodiment of the present invention. The algorithm according to the present exemplary embodiment carries out a process that begins with an ECG recording step 80, in which physician 30 uses multiple electrodes 48 of catheter 21 to acquire intracardiac ECG signals inside heart 26 that are recorded by recording system 35.

At a pacing set-up step 82, physician 30, or an algorithm, selects two of electrodes 48 to pace heart 26. At a checking step 84, the system responds according to whether the selected electrodes belong to the analogically connected or digitally connected subsets of electrodes.

If the selected electrodes are connected via an analog line (i.e., the selected electrodes belong to the analogically connected subset of electrodes), the apparatus handles the selection using an existing (e.g., legacy) hardware and procedure, at a pacing step 86.

If, on the other hand, the selected electrodes are connected via a digital line, PIU 52 of the system outputs the identity of the selected electrodes to processor 41, at an electrode identification step 88, and is not further involved.

Once pacing is initiated and electrode identity is known to be that of electrodes connected via a digital line, physician 30, or an algorithm, operates pacing unit 37 to output pacing signals via dedicated analog line 74, at an outputting pacing signals step 90.

At pacing signal detection step 92, pacing detection circuit 55 detects the pacing signals and responsively triggers processor 41.

Once triggered (at a step 94) by pacing detection circuit 55, processor 41 commands a switching assembly, such as comprising relays 51 inside dongle 50, to switch the selected electrodes from the digital line (70) to the dedicated analog pacing line (110), at a switching step commanding 96.

Responsively, the switching assembly inside dongle 50 switches the selected electrodes as commanded to apply pacing, at a pacing application step 98.

The example flow chart shown in FIG. 3 is chosen purely for the sake of conceptual clarity. For example, the disclosed method may include additional steps, such as verifying contact of selected electrodes with tissue before switching to pacing, and a step of switching the electrodes back to the digital line at the end of pacing.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. An apparatus for cardiac pacing, the apparatus comprising:
    a relay and sampling unit, configured to receive multiple electrocardiogram (ECG) signals that are sensed by respective electrodes in a heart of a patient, to digitize a first subset of the ECG signals, and to forward a second subset of the ECG signals un-digitized over analog lines;
    a pacing unit, configured to output pacing signals;
    a pacing detection circuit, configured to detect the pacing signals and to output a trigger in response to the pacing signals; and
    a processor, configured to:
        receive (i) the trigger and (ii) identities of ones of the electrodes via which the pacing signals are to be applied; and
        in response to identifying that the electrodes, via which the pacing signals are to be applied, are currently associated with the digitized ECG signals, to instruct the relay and sampling unit to switch the identified electrodes to the analog lines for transferring the pacing signals.

2. The apparatus according to claim 1, and comprising a patient interface unit (PIU), which is configured to accept and store the identities of the electrodes via which the pacing signals are to be applied, and wherein the processor is configured to, once triggered by the pacing detection circuit, read the identities from the PIU.

3. The apparatus according to claim 2, wherein the relay and sampling unit is comprised in a dongle that connects the electrodes to the PIU.

4. The apparatus according to claim 1, wherein the pacing detection circuit is further configured to detect that the pacing signals stopped, and in response trigger the processor, and wherein the processor is further configured, once triggered, to command the relay and sampling unit to switch the selected electrodes from the analog lines to digital lines.

5. A method for cardiac pacing, the method comprising:
    in a relay and sampling unit, receiving multiple electrocardiogram (ECG) signals that are sensed by respective electrodes in a heart of a patient, digitizing a first subset of the ECG signals, and forwarding a second subset of the ECG signals un-digitized over analog lines;
    outputting pacing signals using a pacing unit;
    detecting the pacing signals and outputting a trigger in response to the pacing signals;
    receiving in a processor (i) the trigger and (ii) the identities of the electrodes via which the pacing signals are to be applied; and
    in response to identifying that the electrodes, via which the pacing signals are to be applied, are currently associated with the digitized ECG signals, instructing the relay and sampling unit to switch the identified electrodes to the analog lines for transferring the pacing signals.

6. The method according to claim 1, and comprising, upon detecting that the pacing signals stopped, switching the selected electrodes from the analog lines to digital lines.

* * * * *